United States Patent [19]

Gedridge, Jr.

[11] Patent Number: 5,371,257

[45] Date of Patent: Dec. 6, 1994

[54] PREPARATION OF DIISOPROPYL STIBINES AND USE THEREOF

[76] Inventor: Robert Gedridge, Jr., 437 S. Sunland St., Ridgecrest, Calif. 93555

[21] Appl. No.: 159,964

[22] Filed: Nov. 30, 1993

[51] Int. Cl.$^5$ .................... C07F 9/90; C23C 16/00
[52] U.S. Cl. .................... 556/70; 427/252
[58] Field of Search .......... 556/70; 156/610, 613, 156/614; 427/252

[56] References Cited

PUBLICATIONS

Gedridge, Jr. et al., Chem. Mater., vol. 5, No.7, pp.979–982 (1993).

Shin et al., Journal of Crystal Growth, vol. 132, No. 3/4, pp. 371–376 (1993).

*Primary Examiner*—Paul F. Shaver
*Assistant Examiner*—Porfirio Nazario-Gonzalez
*Attorney, Agent, or Firm*—Robert J. Hampsch; Melvin J. Sliwka; John L. Forrest, Jr.

[57] ABSTRACT

The new compound diisopropyl stibine is prepared by reacting an diisopropyl antimony halide with a hydride or deuteride transferring agent. The reaction is preferably carried out below about 0° C., in an inert atmosphere, under darkened conditions. The diisopropyl stibine is used as a precursor in forming antimony-containing semiconductor material by chemical vapor deposition.

14 Claims, No Drawings

PREPARATION OF DIISOPROPYL STIBINES AND USE THEREOF

BACKGROUND OF THE INVENTION

The present invention relates to a new antimony compound, more particularly to an organoantimony compound and its use in chemical vapor deposition processes to produce antimony-containing semiconductor materials.

A variety of semiconductor systems containing antimony have been investigated for applications in infrared detectors, high speed devices, optoelectric devices, and magnetic position sensors.

Antimony-containing binary materials, e.g. InSb and GaSb, as well as ternary and quaternary materials, e.g. $InAs_{1-x}Sb_x$ and $InAs_{1-x-y}Sb_yBi_x$, have been grown heteroepitaxially by organometallic vapor phase epitaxy (OMVPE), a high throughput technique for the production of high quality semiconductor materials from organometallic precursors such as organoantimony compounds.

Certain semiconductor materials have been grown by OMVPE using trimethylantimony or triethylantimony as the organoantimony source compound. Attempts at low growth temperatures resulted in significant problems due to the incomplete pyrolysis of these organoantimony compounds.

An alternative organoantimony precursor for OMVPE is needed which has a lower pyrolysis temperature than the above trimethyl and triethyl antimony compounds. It is also important that such alternative organoantimony precursor pyrolyze with minimal unintentional impurity incorporation. Recently, triisopropylantimony, $((CH_3)_2CH)_3Sb$, was used to grow epitaxial InSb films at temperatures as low as 300° C. However, triisopropylantimony has a low vapor pressure in comparison to trimethylantimony and very low film growth rates resulted. An organoantimony precursor with a higher vapor pressure and a low decomposition temperature is still needed.

It has been demonstrated that the presence of one or more hydrogens bonded to the Group V precursor helps minimize unintentional carbon incorporation into the semiconductor film. However while Group V hydrides such as $AsH_3$ and $PH_3$ are commonly used with Group III trialkyls ($R_3M$: M=Al, Ga, In; R=Me and Et) in the growth of III/V semiconductors, $SbH_3$ is unstable at room temperature and is inconvenient to use since it is not commercially available and must be generated at the place of use. A few primary ($RSbH_2$) and secondary stibines ($R_2SbH$) have been reported, they are unstable and not commercially available. This contrasts with the primary and secondary phosphines and arsines which are stable and commercially available. Furthermore, problems associated with toxicity, high pressure gas storage hazards, transportation restrictions, and high temperatures required for the pyrolysis of these Group V hydrides have resulted in the development of alternates non-hydride Group V source compounds for OMVPE. Since $SbH_3$ is unstable and inconvenient to use, trimethylantimony and triethylantimony are the conventional Sb source compounds used in OMVPE.

The use of Bi in IR detectors has shown to be useful in reducing the band gap of such detectors; however, higher growth temperatures (400° C. and above) results in poor Bi-containing-film morphology. In order to minimize the tendency of the Bi to phase separate and to limit the diffusion in these alloys by lowering the film growth temperature, an alternative organoantimony precursor for OMVPE is needed which has a lower pyrolysis temperature than trimethylantimony.

The availability of alternative Sb source compounds for OMVPE could greatly enhance the development of antimony-containing semiconductor materials. Development of new Sb source compounds for chemical vapor deposition processes is of interest for lowering the film-growth temperature of Sb-containing semiconductor materials and altering the chemistry to minimize unintentional impurities.

One object of the invention is the provision of an improved organoantimony source compound for antimony-containing semiconductor materials.

Another object is to provide an organoantimony precursor for OMVPE for the production of antimony-containing semiconductor materials having a higher vapor pressure and a lower decomposition temperature than organoantimony precursors heretofore used.

Still another object is the provision of a novel organoantimony precursor which pyrolyses with minimal unintentional impurity incorporation into the antimony-containing semiconductor material.

A still further object is to provide a process for preparing such antimony source compound or precursor for production of antimony-containing semiconductor materials.

Yet another object is the provision of a process of forming an antimony-containing semiconductor material by chemical vapor deposition, using an improved organoantimony source compound.

SUMMARY OF THE INVENTION

The above objects and advantages can be achieved according to the invention by the provision of the new compound diisopropyl stibines, $((CH_3)_2CH)_2SbY$ (where Y =Hydrogen or Deuterium). This compound can be conveniently prepared by reacting diisopropyl antimony halide $((CH_3)_2CH)_2SbX$ with a hydride or deuteride transfer agent at cool temperatures in a suitable solvent under an inert atmosphere and in the absence of light.

Also, according to the invention, an improved process is provided for forming antimony-containing semiconductor materials using chemical vapor deposition. In the process a diisopropyl stibine is used as the source of antimony. The process can be used in forming III/V Sb-containing semiconductor materials and can also be used to introduce Sb as a dopant in II/VI and IV semiconductor materials.

DETAILED DESCRIPTION OF THE INVENTION AND PREFERRED EMBODIMENTS

The new compound diisopropyl stibine is prepared according to the reaction scheme noted below:

$((CH_3)_2CH)_2SbX$ +  [1]

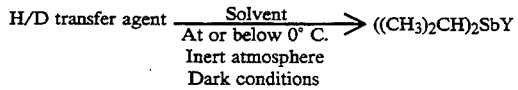

where X is a halide, and where Y=Hydrogen or Deuterium

The diisopropyl stibines, $((CH_3)_2CH)_2SbY$ (where Y=H or D), can be prepared and isolated by reacting diisopropyl antimony halide $((CH_3)_2CH)_2SbX$, where X is a halide, with a hydride or deuteride transferring agent, at low temperatures, in a suitable solvent such as diethyl ether under an inert atmosphere such as argon in the absence of light.

The diisopropyl antimony halide can be prepared by methods known in the art. A preferred method is illustrated by the reaction scheme noted below:

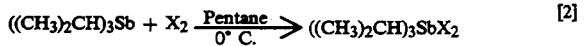

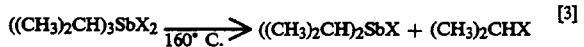

In the preferred practice, purified tri isopropylantimony, $((CH_3)_2CH)_3Sb$, is reacted with one equivalent of the dihalide, $X_2$, to give triisopropylantimony dihalide, $((CH_3)_2CH)_3SbX_2$, as an intermediate in equation 2. Triisopropylantimony dihalide is then heated to 160° C. for two hours at 90 torr pressure. Diisopropylantimony halide is then fractionally vacuum distilled as shown in equation 2.

All preparation, isolation, and purification of the air-sensitive product is carried out using inert-atmosphere techniques.

All preparation, isolation, and purification of the light-sensitive product is carried out using light-blocking techniques.

In the above reactions, a molar ratio of the diisopropyl antimony halide and the hydride/deuteridetransferring agent ranging from about 1:1 to about 1:2 is employed. Any hydride or deuteride transfer reagent, e.g., $LiAlX_4$, $AlY_3N(CH_3)_3$, $LiY$, $CaY_2$ etc., (where X=H or D), can be used. Solvents used during synthesis must be thoroughly free of oxygen or water. While diethyl ether is the preferred solvent in which to carry out the reactions above, other oxygen and water-free organic solvents, e.g. tetrahydrofuran, other ethereal solvents, or some combination of solvents, can be employed.

The reactions as illustrated in equation [1] above, for the production of diisopropyl stibine are commenced at low temperatures below 0° C., preferably about −78° C. If the reaction occurs at temperatures above about 0° C., more of the unwanted tetraisopropylstibine and hydrogen side products will form. If the reaction is exposed to sufficient room light at low temperatures, or at room temperatures, more of the unwanted side products will form.

Pressure is not a critical factor in carrying out reactions (1) and (2) above, and generally ambient pressure is employed, although higher or lower pressures can be utilized in the preparation of diisopropyl stibines.

Diisopropyl stibine, $((CH_3)_2CH)_2SbH$, is a colorless liquid at room temperature. Diisopropyl stibine is extremely air- and light-sensitive and requires its preparation, isolation and purification under an inert atmosphere, e.g. argon, nitrogen, helium in the absence of light. Diisopropyl stibine has a vapor pressure approximately 6 torr (mm Hg) at 32°–33° C. and 15 torr at 43° C.

Diisopropyl stibine, $((CH_3)_2CH)_2SbH$, can be used as an alternative precursor to the OMVPE growth of antimony-containing, e.g. III/V Sb-containing, semiconductor materials. Diisopropyl stibine can also be used to introduce Sb as a dopant in II/VI and IV semiconductor materials. Diisopropyl stibine can decompose at lower temperatures than trimethylantimony due to the reduced bond strength of the H-Sb bond. Diisopropyl stibine is an alternative Sb source compound with a useful vapor pressure that can be used at lower film growth temperatures and pyrolyses more efficiently at higher growth temperatures than trimethylantimony.

III/V antimony-containing semiconductor materials can be binary (2-element), ternary (3-element) or quaternary (4-element) semiconductor materials containing at least one element from group IIIB and at least one element from group VB of the periodic table, at last one of such elements from group VB being antimony.

Diisopropyl stibine is used to introduce antimony into semiconductor materials following methods known in the art, generally described as follows: Hydrogen or some other carrier gas, e.g., helium, nitrogen, is bubbled through liquid Diisopropyl stibine in a container. The hydrogen transports the diisopropyl stibine in vapor phase into a reactor for chemical vapor deposition (e.g., OMVPE). The vapor stream comes into contact with a heated substrate, which can be any semiconductor substrate such as Si, GaAs, InSb, GaP, InP or InAs. This can be done at low, atmospheric or high pressures.

In case of a binary semiconductor, containing antimony, for example, there are two lines entering the reaction zone each with a gas saturated with a precursor of the two elements, one of which is diisopropyl stibine. Such gases contact the heated substrate and deposit a semiconductor on the substrate. Where diisopropyl stibine is used as a precursor to introduce antimony as a dopant into semiconductor materials, substantially the same process as noted above is employed, but at a low concentration of the diisopropyl stibine in the gas phase, so that the antimony is not a major component of the resulting semiconductor compound, but is present in sufficient concentration to provide suitable desired electrical properties.

EXAMPLE 1

General Procedures

Organoantimony compounds should be handled with extreme caution since they are toxic. Organic solvents were distilled under Ar from sodium/benzophenone. Synthesis was carried out under purified Ar using inert atmosphere techniques. Air- and moisture-sensitive materials were transferred inside a $N_2$-filled Vacuum Atmospheres glove box. $SbCl_3$ (99.99% metal basis) was purchased from Alfa. Isopropyl Grignard, $Br_2$, and $LiAlH_4$ reagents were purchased from Aldrich and used as received. NMR spectra were recorded on $C_6D_6$ solutions with an Bruker AMX-400 spectrometer. $^{13}C$ spectra were obtained at 100.6 MHz with $^1H$-coupled $^{13}C$ spectra obtained under gated decoupling conditions.

SYNTHESIS of $((CH_3)_2CH)_2SbH$

To a stirring slurry of 0.330 g(8.69 mmol) of $LiAlH_4$ in 15 mL of $Et_2O$ at −78° C. was added dropwise (drop time=30 min), in the dark, a solution of 2.502 g (8.693 mmol) of $((CH_3)_2CH)_2SbBr$ in 15 mL of $Et_2O$. After the addition was complete, the slurry was warmed to room temperature slowly and stirred at room temperature overnight. An off-white slurry resulted. All the volatiles from the slurry were collected in a liquid nitrogen trap under vacuum. The solvent from the condensed colorless fraction was fractionally distilled off using a 35°–40° C. water bath. ((CH$_3$)$_2$CH)$_2$SbH, an extremely air- and light-sensitive colorless liquid, was fractionally distilled at 32°–33° C. at 6 torr (1.010 g, 56% yield based on ((CH$_3$)$_2$CH)$_2$SbBr). ((CH$_3$)$_2$CH)$_2$SbH, showed no evidence of decomposition after storage for four days in the dark at 0° C. ((CH$_3$)$_2$CH)$_2$SbH starts to decomposes within minutes after exposure to light. $^1$H NMR (C$_6$D$_6$): 3.53 ppm (t of m, 1 H, Sb—H. $^3J_{HH}$=3.6, $^4J_{HH}$=0.5 Hz) 2.05 ppm (septet of d 3H CH—Sb, $^3J_{HH}$=3.6, $^3J_{HH}$=7.3 Hz), 1.41 ppm (d, 9H, CH$_3$, $^3J_{HH}$=7.3 Hz) 1.27 ppm (d, 9H, CH$_3$, $^3J_{HH}$=7.3 Hz). $^{13}$C NMR (C$_6$D$_6$): 25.5 ppm (q of m, CH$_3$, $^1J_{CH}$=126 Hz), 24.2 ppm (q of m, CH$_3$, $^1J_{CH}$=126 Hz) 15.2 ppm (d of m, CH, $^1J_{CH}$=134 Hz). Anal. Calcd for C$_6$H$_{15}$Sb: C, 34.49; H, 7.24; Sb, 58.27. Found: C, 34.45; H, 7.10; Sb, 58.05.

EXAMPLE 2

General Procedures

Purified diisopropylantimony hydride, ((CH$_3$)$_2$CH)$_2$SbH, was loaded into a clean glass container that is similar to typical stainless steel OMVPE bubblers used in semiconductor film growth. ((CH$_3$)$_2$CH)$_2$SbH was pyrolyzed in a horizontal OMVPE reactor with silicon substrates mounted on a graphite susceptor that was inductively heated with an RF generator. The Sb films were deposited on Si (100) and Si (111) substrate using hydrogen and argon carrier gases. Flow rates used were 13 sccm and 40 sccm. Highly crystalline Sb films were deposited on Si substrates as low as 200° C. and 350° C. in hydrogen. Auger Electron Spectroscopy of films provided detailed micrographs and analysis showed no carbon within the detectable limits of the instrument.

Detailed descriptions and results of these growth studies can be found in an article by J. Shin, et al., entitled *Diisopropylantimonyhydride (DIPSbH) for low temperature epitaxial growth of InSb, Journal of Crystal Growth,* 132 (1993) pages 371–376.

From the foregoing, it is seen that the present invention provides for the preparation and isolation of the novel compound diisopropyl stibine, ((CH$_3$)$_2$CH)$_2$SbY, where Y=Hydrogen or Deuterium.

Diisopropyl stibine is an alternative improved antimony precursor for forming antimony-containing semiconductor materials using chemical vapor deposition techniques, e.g. organometallic vapor phase epitaxy. In the process diisopropyl stibine is used as a source of antimony. The process can be used in forming III/V antimony-containing semiconductor materials, and can also be used to introduce antimony as a dopant in II/VI and IV semiconductor materials.

Since various changes and modifications can be made in the invention without departing from the spirit of the invention, the invention is not to be taken as limited except by the scope of the appended claims.

What is claimed is:

1. The compound having the formula ((CH$_3$)$_2$CH)$_2$SbY, where Y is Hydrogen or Deuterium.

2. A process for preparing the compound having the formula ((CH$_3$)$_2$CH)$_2$SbY, where Y is Hydrogen or Deuterium, which comprises the following steps:
    A) reacting diisopropyl antimony halide with a hydride/deuteride transferring agent;
    B) recovering ((CH$_3$)$_2$CH)$_2$SbY from the reaction mixture.

3. The process of claim 2, employing approximately one equivalent of diisopropyl antimony halide and approximately one equivalent of hydride/deuteride transferring agent.

4. The process of claim 2, the reaction taking place at a temperature of 0° C. or lower.

5. The process of claim 2, the reaction and recovery taking place in an inert atmosphere.

6. The process of claim 2, the reaction taking place in an oxygen-free, water-free, organic solvent.

7. The process of claim 2, wherein the entire process is performed using light-blocking techniques.

8. The process of claim 2, the reaction taking place at a temperature ranging from about −78° C. to about −50° C.

9. The process of claim 6, wherein the solvent is one or more organic solvents selected from the group consisting of: ethereal solvents and tetrahydrofuran..

10. The process of claim 2, wherein the hydrogen/Deuterium transferring agent is selected from the group consisting of: LiAlY$_4$, LiY, CaY$_2$ and AlY$_3$N(CH$_3$)$_3$, where Y is Hydrogen or Deuterium.

11. The process of claim 2, wherein the diisopropyl antimony halide is selected from the group consisting of the bromide, chloride and iodide.

12. The process of claim 5, wherein the inert atmosphere is argon.

13. In a process of forming an antimony-containing semiconductor material by chemical vapor deposition, the improvement comprising using ((CH$_3$)$_2$CH)$_2$SbY as a source of antimony, where Y is Hydrogen or Deuterium.

14. The process of claim 13, which comprises bubbling a carrier gas thorough liquid ((CH$_3$)$_2$CH)$_2$SbY, and transporting the ((CH$_3$)$_2$CH)$_2$SbY with the carrier gas to a heated substrate and depositing Sb from said ((CH$_3$)$_2$CH)$_2$SbY, and additional elements on said substrate from groups selected from Groups II, III, V and VI of the periodic table to form III/V Sb-containing semiconductor materials or to provide Sb as a dopant in II/VI and IV semiconductor materials.

* * * * *